(12) United States Patent
Du et al.

(10) Patent No.: US 12,351,785 B2
(45) Date of Patent: Jul. 8, 2025

(54) PICHIA KUDRIAVZEVII AND MULTIFUNCTIONAL COMPLEX MICROBIAL INOCULANT AND USE THEREOF

(71) Applicant: Jiangnan University, Wuxi (CN)

(72) Inventors: Hai Du, Wuxi (CN); Yan Xu, Wuxi (CN); Hongxia Zhang, Wuxi (CN); Nan Deng, Wuxi (CN)

(73) Assignee: Jiangnan University, Wuxi (CN)

( * ) Notice: Subject to any disclaimer, the term of this patent is extended or adjusted under 35 U.S.C. 154(b) by 478 days.

(21) Appl. No.: 17/748,304

(22) Filed: May 19, 2022

(65) Prior Publication Data

US 2022/0290079 A1    Sep. 15, 2022

Related U.S. Application Data

(63) Continuation of application No. PCT/CN2021/078142, filed on Feb. 26, 2021.

(30) Foreign Application Priority Data

Feb. 28, 2020 (CN) .......................... 202010129643.1

(51) Int. Cl.
| | |
|---|---|
| C12N 1/16 | (2006.01) |
| A01N 63/32 | (2020.01) |
| A01P 1/00 | (2006.01) |
| A21D 8/04 | (2006.01) |
| A23B 2/783 | (2025.01) |
| A23C 19/032 | (2006.01) |
| A23L 27/50 | (2016.01) |
| C12G 1/022 | (2006.01) |
| C12G 3/022 | (2019.01) |
| C12R 1/84 | (2006.01) |

(52) U.S. Cl.
CPC ........... *C12G 1/0203* (2013.01); *A01N 63/32* (2020.01); *A01P 1/00* (2021.08); *A21D 8/047* (2013.01); *A23B 2/783* (2025.01); *A23C 19/0325* (2013.01); *A23L 27/50* (2016.08); *C12G 3/022* (2019.02); *C12N 1/165* (2021.05); *A23V 2002/00* (2013.01); *C12G 2200/05* (2013.01); *C12R 2001/84* (2021.05)

(58) Field of Classification Search
CPC ..................................................... C12N 1/165
See application file for complete search history.

(56) References Cited

FOREIGN PATENT DOCUMENTS

| | | |
|---|---|---|
| CN | 107287127 A | 10/2017 |
| CN | 109897807 A | 6/2019 |
| CN | 111254085 A | 6/2020 |
| KR | 20140034644 A | 3/2014 |

OTHER PUBLICATIONS

Xu,Dai et. al. "Screening of a high-yield phenylethanol yeast and optimization of its cultural conditions" Science and Tech of Food Industry. Dec. 31, 2017. V5,Issue 38, p. 151-158.
Silvana M. del M naco et. al. "Selection and characterization of a Patagonian Pichia kudriavzevii for wine deacidification" Journal of Applied Microbiology. Aug. 31, 2014. V2, Issue 117, p. 451-464.

*Primary Examiner* — Ruth A Davis
(74) *Attorney, Agent, or Firm* — IPRO, PLLC

(57) ABSTRACT

The present disclosure discloses a *Pichia kudriavzevii* and a multifunctional complex microbial inoculant and use thereof, and belongs to the technical field of bioengineering. The *Pichia kudriavzevii* of the present disclosure has a degrading ability of lactic acid as high as 12.69 g·L$^{-1}$, which is 2.04 times that of a type strain. At the same time, the strain can also metabolize ethanol and has an OD$_{600}$ of 4.48 after fermentation in a sorghum juice medium at 30° C. and 200 rpm for 3 d. The *Pichia kudriavzevii* could completely consume 58 g·L$^{-1}$ of glucose in the sorghum juice medium after 60 h of fermentation and produce 13.06 g·L$^{-1}$ of ethanol. The *Pichia kudriavzevii* degrades lactic acid and can relieve a lactic acid pressure of a fermentation system and enable *Saccharomyces cerevisiae* to grow and metabolize to produce wine. In addition, the strain and the microbial inoculant thereof can inhibit the production of filamentous fungi and geosmin and have important use prospects for maintaining homeostasis of a fermentation system and food preservation.

4 Claims, 14 Drawing Sheets

The second row of PDA plates were coated with *Pichia*

PICHIA KUDRIAVZEVII AND MULTIFUNCTIONAL COMPLEX MICROBIAL INOCULANT AND USE THEREOF

TECHNICAL FIELD

The present disclosure provides a *Pichia kudriavzevii* and a multifunctional complex microbial inoculant and use thereof, and belongs to the technical field of bioengineering.

BACKGROUND

Baijiu is a typical traditional fermented food in China. In an anaerobic fermentation process of the baijiu, acid-producing microorganisms such as lactic acid bacteria and the like metabolize to produce a large amount of acid substances, such that difficult-to-volatile acid substances in fermented grains are continuously accumulated. As a main organic acid in the fermented grains, the lactic acid has the content of 20-40 g.kg$^{-1}$ fermented grains of soy sauce-aroma baijiu and the content of 20-30 g.kg$^{-1}$ fermented grains of strong-aroma baijiu separately. The accumulation of the lactic acid increases acidity of the fermented grains in the baijiu fermentation, such that microorganisms stop growing and even die. The undissociated form of the lactic acid is lipophilic, thus the lactic acid can pass through a cell membrane and flow into cytoplasm by simple diffusion. In the near neutral cytoplasm, the lactic acid dissociates and releases protons (H$^+$) and lactate ions. Since the ions are charged, they cannot pass through a hydrophobic phospholipid bilayer and thus accumulate inside cells, leading to a decrease of intracellular pH (pHi) and destruction of a cytoplasmic anion pool. The protons and the anions have destructive effects on cell membranes, ribosomal ribonucleic acid (RNA), deoxyribonucleic acid (DNA) and active enzymes, thereby damaging cell viability and affecting growth and metabolism of microorganisms.

Yeast is an important microorganism in a brewing process of the baijiu and important for promoting a fermentation process. At the same time, volatile flavor compounds produced by metabolism are important factors for affecting styles and quality of the baijiu. In a brewing process of the soy sauce-aroma baijiu, a large amount of yeast is enriched and propagated through a stacking fermentation process and enters a cellar to participate in an anaerobic fermentation process. A structure composition and a change rule of the yeast community in the fermentation of the soy sauce-aroma baijiu are studied by using an MiSeq sequencing technology and a real-time qPCR method. Studies show that in addition to *Saccharomyces cerevisiae*, *Pichia kudriavzevii* is the dominant yeast in the fermentation process of the baijiu. The *Pichia kudriavzevii* makes a considerable contribution to the flavor of the baijiu and can produce esters, higher alcohols and volatile acids. However, a domestic research on the *Pichia kudriavzevii* in the baijiu is still limited to separation and identification of single strains, fermentation characteristics of the single strains under pure culture, and the like. There is no deep research on a response and a degradation mechanism of the *Pichia kudriavzevii* to growth inhibitory factors (such as lactic acid and the like) in the fermentation process.

Lactic acid is a common metabolite and a growth inhibitor in a fermentation process of fermented food and beverages. In the fermentation process of various-aroma baijiu, the lactic acid is a common organic acid with the highest content. In the fermentation process of the soy sauce-aroma baijiu, the lactic acid has a concentration of 28.05±4.75 g.kg$^{-1}$ to 36.20±6.20 g.kg$^{-1}$ fermented grains. Since the content of the lactic acid increases in a later stage of fermentation, the high content of the lactic acid may inhibit growth of these core yeasts and thus inhibit production of ethanol by these core yeasts. The high-concentration lactic acid affects yeast in the following two ways. On the one hand, the high-concentration lactic acid in the fermented grains produces high-concentration protons, which directly affect a cell wall structure and alter conformation of cell membrane proteins. On the other hand, the fermented grains has a pH stabilized at 3.50, the lactic acid has a pKa of 3.86 at a room temperature, and in the fermented grains with a pKa lower than that of the lactic acid, undissociated lactic acid is dominant and permeates a cell membrane by simple diffusion. This directly affects pH homeostasis in the cells and weak acids also have a direct effect on lipid tissues and functions of the cell membrane. In addition, since the baijiu is usually subjected to repeated batch fermentation, particularly the soy sauce-aroma baijiu has multiple rounds and a long period of a brewing process, the difficult-to-volatile acid substances in the fermented grains are continuously accumulated.in the anaerobic fermentation process of the cellar. Besides, the lactic acid is difficult to volatilize and can be remained in the fermented grains in a distillation process, which is unfavorable for a subsequent fermentation of the baijiu. In a spontaneous fermentation process of the baijiu, it is very important to artificially regulate and control excessively high lactic acid in the fermented grains by using a biological acid-reducing method, such that a microorganism capable of tolerating the high lactic acid and degrading the lactic acid is urgently needed.

Based on the urgent need, in an early production stage of strong-aroma baijiu, "increasing ethyl hexanoate and reducing ethyl lactate" is mainly realized by improving a distillation process and the like, but the method has a limited use range. In the soy sauce-aroma baijiu, yeast capable of tolerating lactic acid is mainly found for baijiu fermentation in the high-lactic acid environment, but the method is difficult. It is very important for improving the quality of the baijiu by studying an acid-reducing function of the yeast. The *Pichia kudriavzevii* is a non-*Saccharomyces cerevisiae* dominant in various baijiu. Therefore, to obtain the *Pichia kudriavzevii* capable of degrading lactic acid is important for producing fermented food and has important value for improving the yield and the quality of the fermented products.

In addition, for the fermented food using the *Pichia kudriavzevii* as a main functional microorganism, it is also needed for maintaining homeostasis of flora and/or inhibiting odor and/or inhibiting growth of undesired microorganisms.

SUMMARY

In order to solve the above problems, the present disclosure provides a *Pichia kudriavzevii* DC-16. The *Pichia kudriavzevii* DC-16 has been deposited in the China General Microbiological Culture Collection Center whose address is No. 3, Courtyard 1, West Beichen Road, Chaoyang District, Beijing on Jan. 13, 2020 and has a deposit number of CGMCC NO. 19337.

The *Pichia kudriavzevii* CGMCC NO. 19337 of the present disclosure (1) can tolerate high-concentration lactic acid and efficiently degrade lactic acid; (2) can relieve a lactic acid pressure of a fermentation system; (3) can enable *Saccharomyces cerevisiae* to grow and metabolize to produce wine when combined with the *Saccharomyces cerevisiae*; (4) can obviously inhibit undesired microorganisms (molds) and can be used in the fields of food fermentation, preservation and the like; and (5) can effectively inhibit odor, such as inhibiting geosmin in fermentation of Daqu and fermented grains.

The *Pichia kudriavzevii* of the present disclosure is derived from a baijiu brewing system and can also be used for a baijiu fermentation system. In the mixed microorganism fermentation system for brewing the baijiu, *Saccharomyces cerevisiae* and non-*Saccharomyces cerevisiae* play important roles in a structure and functions. The present disclosure further analyzes a lactic acid tolerance of the *Saccharomyces cerevisiae* and non-*Saccharomyces cerevisiae* and a mechanism thereof in the baijiu brewing system. The CGMCC NO. 19337 strain of the present disclosure has beneficial effects on ecological restoration, flora homeostasis maintenance, undesired microorganism growth and the like, helps to maintain stability of fermentation ability of the yeast during the fermentation process of the baijiu, improves the quality of the baijiu, and enables production of the baijiu to be standardized, precise and controllable. Meanwhile, the CGMCC NO. 19337 of the present disclosure can also be used for other fermented food taking the *Pichia kudriavzevii* as a main functional microorganism and a preparation of the fermented food, such as baijiu brewing, grape wine brewing, sake fermentation, cheese production, dough fermentation, soybean paste fermentation, and the like.

The present disclosure also provides a method for degrading lactic acid. The Pichia kudriavzevii DC-16 is used as a fermentation strain and degrades lactic acid during a fermentation process.

In one embodiment of the present disclosure, the fermentation is conducted by using a sorghum juice medium as a fermentation medium.

In one embodiment of the present disclosure, the sorghum juice medium is obtained by adding amylase into sorghum and water at a ratio of 1:4 (M:V) for cooking and liquefaction, adding a saccharifying enzyme for saccharification at 60° C., filtering and centrifuging, and adjusting the sugar content to 7° Bx.

In one embodiment of the present disclosure, the degradation is specifically conducted as follows: inoculating the *Pichia kudriavzevii* DC-16 at an inoculum size (v:v) of 5-10% in the lactic acid-containing sorghum juice medium and culturing at 28-32° C. and 180-220 rpm for 60-100 h.

The present disclosure also provides a method for degrading lactic acid. The *Pichia kudriavzevii* DC-16 and an *Saccharomyces cerevisiae* DC-3 are used as fermentation strains and degrade lactic acid during a fermentation process. The *Saccharomyces cerevisiae* DC-3 has been deposited in the China General Microbiological Culture Collection Center whose address is No. 3, Courtyard 1, West Beichen Road, Chaoyang District, Beijing on Jan. 13, 2020 and has a deposit number of CGMCC NO. 19336.

In one embodiment of the present disclosure, the degradation is specifically conducted as follows: inoculating the *Pichia kudriavzevii* DC-16 and the *Saccharomyces cerevisiae* DC-3 into the sorghum juice medium, adding lactic acid, and culturing at 28-32° C. and 180-220 rpm for 60-100 h.

In one embodiment of the present disclosure, the *Pichia kudriavzevii* DC-16 and the *Saccharomyces cerevisiae* DC-3 both have an initial inoculation concentration of $10^7$-$10^8 \cdot mL^{-1}$ and have an inoculation concentration ratio of 1:1.

The present disclosure also provides a microbial preparation containing the *Pichia kudriavzevii* DC-16.

The present disclosure also provides the *Pichia kudriavzevii* DC-16 or a microbial preparation in the fields of food or wine brewing. For example, practical use of the *Pichia kudriavzevii* DC-16 microbial preparation during a fermentation process of soy sauce-aroma baijiu. In a process of mixing Daqu, after yeast liquid of $10^6$ CFU/kg$^{-1}$ fermented grains is added, stacking fermentation is conducted and at the end of the stacking fermentation, the lactic acid content in the fermented grains is significantly reduced by 75%.

In one embodiment of the present invention, the use is suitable for food fermentation and preservation; and the *Pichia kudriavzevii* DC-16 or the microbial preparation has a significant effect on inhibiting undesired microorganisms (molds) and can be used in the fields of food fermentation and preservation.

In one embodiment of the present disclosure, the use is adding the *Pichia kudriavzevii* DC-16 or the microbial inoculant to a team with severe agglomeration during a fermentation process of soy sauce-aroma baijiu. Results show that in an in-situ fermented grains, agglomeration is serious and the ethanol yield is significantly reduced. In an intervention experiment with the *Pichia kudriavzevii*, the fermented grains are good and do not show obvious agglomeration and mildew.

In one embodiment of the present disclosure, the used is for inhibiting odor.

In one embodiment of the present disclosure, the used is for inhibiting geosmin in a production process of geosmin. The *Pichia kudriavzevii* DC-16 has a significant inhibitory effect on geosmin-producing *Streptomyces albus*. In addition, a pilot test is conducted during a Daqu-making process. Results show that the content of the geosmin is the highest in a control group on the 20th day and reaches 9.75 μg/kg; and the content of the geosmin is 6.23 μg/kg in a group containing a biological inoculum, which is significantly lower than that of the control group. The microorganism has an average inhibitory rate of the geosmin of 14.4% in rind of Daqu and a final inhibitory rate of 36.1%.

Beneficial Effects of the Present Disclosure:

The present disclosure provides a *Pichia kudriavzevii* strain. The *Pichia kudriavzevii* strain has a degrading ability of lactic acid as high as 12.69 g·L$^{-1}$, which is 2.04 times that of a type strain. At the same time, the strain can also metabolize ethanol and has a cell concentration OD$_{600}$ reaching 4.48 after fermentation in a sorghum juice medium at 30° C. and 200 rpm for 3 d; and after fermentation for 60 h, the strain can completely consume 58 g·L$^{-1}$ of glucose in the sorghum juice medium and produce 13.06 g·L$^{-1}$ ethanol. The *Pichia kudriavzevii* degrades lactic acid and can relieve a lactic acid pressure of a fermentation system and enable *Saccharomyces cerevisiae* to grow and metabolize to produce wine. Based on the above characteristics, the *Pichia kudriavzevii* and the inoculum of the present disclosure can be directly used in baijiu fermentation, grape wine fermentation or biofuel production, and can alleviate delayed industrial fermentation or stagnant fermentation caused by excessive accumulation of lactic acid, high acidity, etc. In addition, the strain can also inhibit undesired microorganisms by volatile substances and thus inhibit mold outbreak in a fermentation process. In addition, as a natural microorganism for biological control of geosmin and *Streptomyces*, the strain has a regulating effect on the geosmin in Daqu and the fermentation process.

Deposit of Biological Material

A *Pichia kudriavzevii* DC-16 has been deposited in the China General Microbiological Culture Collection Center whose address is No. 3, Courtyard 1, West Beichen Road, Chaoyang District, Beijing on Jan. 13, 2020 and has a deposit number of CGMCC NO. 19337.

An *Saccharomyces cerevisiae* DC-3 has been deposited in the China General Microbiological Culture Collection Center whose address is No. 3, Courtyard 1, West Beichen Road, Chaoyang District, Beijing on Jan. 13, 2020 and has a deposit number of CGMCC NO. 19336.

DETAILED DESCRIPTION (I) Medium

Figure 1A:
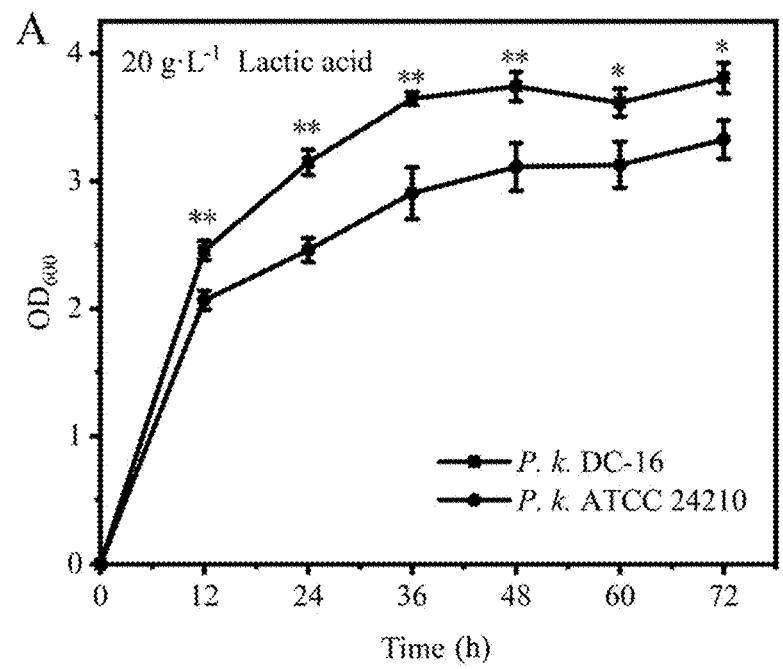
FIG. 1A shows growth curves of an experimental strain and a type strain under 20 g $L^{-1}$ lactic acid.

Enrichment medium: 40 g $L^{-1}$ of lactic acid, 50 g $L^{-1}$ of glucose, 20 g $L^{-1}$ of peptone, 10 g $L^{-1}$ of yeast extract, 2 g $L^{-1}$ of dipotassium hydrogen phosphate, 1 g $L^{-1}$ of sodium chloride, 0.1 g $L^{-1}$ of magnesium sulfate and 0.05 g $L^{-1}$ of manganese sulfate.

Screening medium: 40 g $L^{-1}$ of lactic acid, 50 g $L^{-1}$ of glucose, 20 g $L^{-1}$ of peptone and 10 g $L^{-1}$ of yeast extract.

Sorghum juice medium: adding amylase into sorghum and water at a ratio of 1:4 (M:V) for cooking and liquefaction, adding a saccharifying enzyme for saccharification at 60° C., filtering and centrifuging, and adjusting the sugar content to 7° Bx.

(II) Method for Detecting Content of Lactic Acid

A fermentation broth is filtered through a 0.22-μm organic-phase syringe filter and a filtrate is transferred to a liquid-phase vial. Chromatographic column: Bio-Rad Aminex HPX-87H Ion Exclusion Column and column temperature: 60° C.; detector: UV detector (PDA) and detection wavelength: 210 nm; and mobile phase: 5 mmol $L^{-1}$ $H_2SO_4$ and flow rate: 0.6 mL.min$^{-1}$.

(III) Method for Detecting Content of Ethanol

A fermentation broth is filtered through a 0.22-μm organic-phase syringe filter and a filtrate is transferred to a liquid-phase vial. Chromatographic column: Bio-Rad Aminex HPX-87H Ion Exclusion Column and column temperature: 60° C.; detector: differential refractive index detector (RID); and mobile phase: 5 mmol $L^{-1}$ $H_2SO_4$ and flow rate: 0.6 mL.$min^{-1}$.

Example 1

Screening of Strain

During a fermentation process of soy sauce-aroma baijiu, a strain of lactic acid-resistant *Pichia kudriavzevii* was obtained. A process was as follows.

A sample of fermented grains of a soy sauce-aroma baijiu was collected. 10 g of the sample was weighed and put into a 250-mL conical flask, 90 mL of sterile normal saline was added, glass beads were added and even shaking was conducted. 0.1 mL of a supernatant was pipetted into 100 mL of an enrichment medium, culture was conducted at 30° C. and 200 rpm for 2-4 d, and whether the culture medium was turbid or not was observed; if the culture medium was obviously turbid, 0.1 mL of the enrichment medium was pipetted to 100 mL of a new liquid screening medium, culture was conducted at 30° C. and 200 rpm for 2 d, after culturing for 3-4 times, the medium was diluted on YPD solid medium in a gradient manner, and after culturing for 3-4 d, single colonies were a target strain with an anti-lactic acid property.

Seven single colonies were randomly selected from a plate and inoculated into a sorghum juice liquid medium containing 40 g·$L^{-1}$ of lactic acid and a pH was adjusted to 3.5. Fermentation was conducted at 30° C. and 200 rpm for 3 d. The lactic acid concentration in the fermentation broth was determined and one strain had the highest amount of degrading lactic acid at 12.69 g·$L^{-1}$. The strain was streaked into a slant medium, stored in a glycerol tube and named DC-16.

Example 2

Identification of Strain (1) Colony Characteristics and Cell Morphology

The colony was white, had a rough surface and uniform texture, and was easy to pick. Morphological results by microscopic observation showed that isolated and screened cells were oval and some cells were budding and dividing.

(2) Physiological and Biochemical Characteristics

Figure 4:
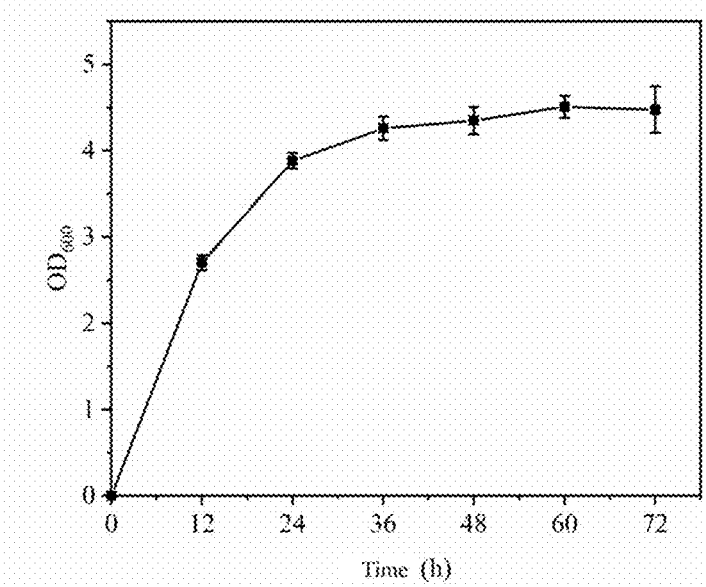
FIG. 4 shows a growth curve of a *Pichia kudriavzevii* DC-16.

DC-16 was inoculated in a sorghum juice medium, fermented at 30° C. and 200 rpm for 1 d, and entered a stationary phase. As shown in FIG. 4, the biomass $OD_{600}$ of the DC-16 could reach 4.48 when fermentation for 3 d.

Figure 5A:
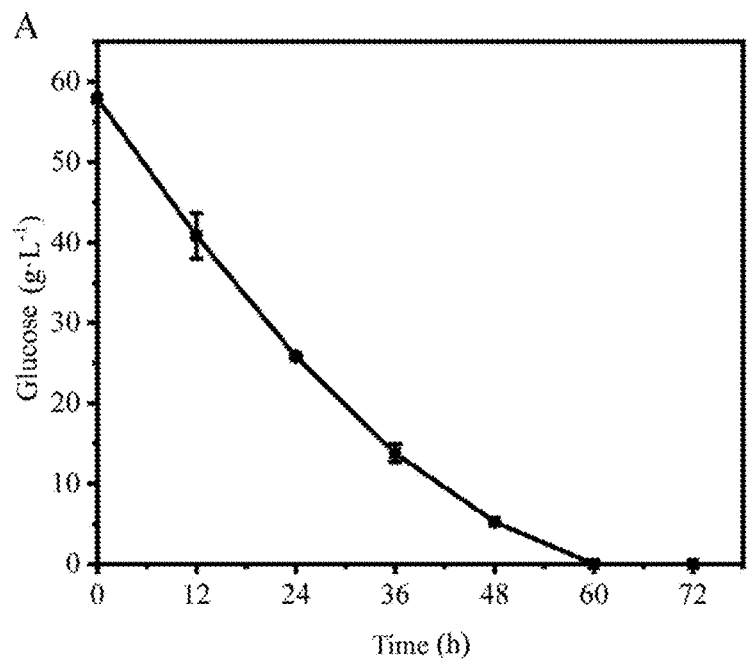
FIG. 5A shows glucose consumption amount of a strain DC-16 under different times.
Figure 5B:
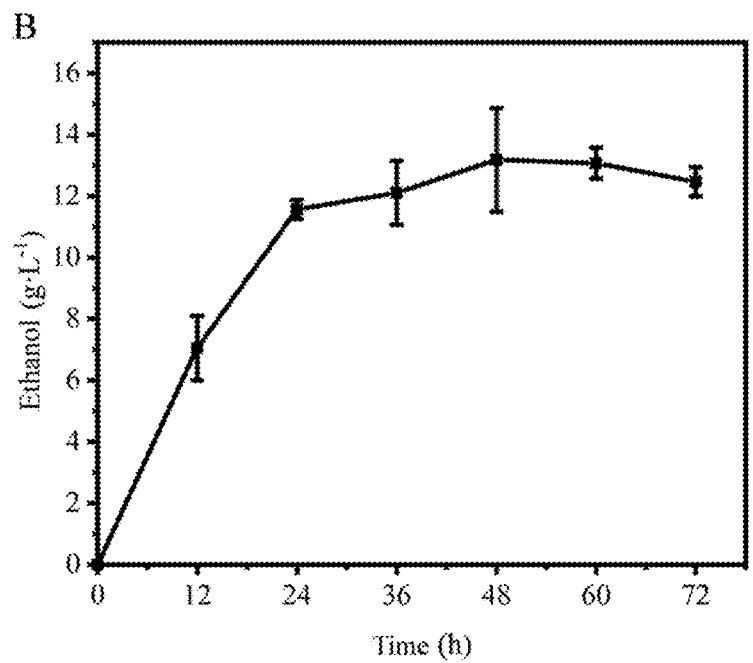
FIG. 5B shows ethanol production amount of a strain DC-16 under different times.

The glucose content in the sorghum juice medium was 58 g·$L^{-1}$. As shown in FIG. 5A and FIG. 5B, the DC-16 could completely consume 58 g·$L^{-1}$ of glucose in the sorghum juice medium after 60 h of fermentation and produce 13.06 g·$L^{-1}$ of ethanol.

(3) Molecular Biological Identification

The strain DC-16 was inoculated into the YPD medium and cultured for 1 d, and the total DNA of the strain was extracted as a PCR template. Yeast ITS universal primers were used for PCR amplification and the selected universal primers were ITS1 and ITS4. PCR amplification conditions: 94° C. for 5 min, 94° C. for 30 s, 55° C. for 30 s and 72° C. for 1 min, a total of 30 cycles; and 72° C. for 10 min. After passing a 1% agarose gel inspection, a PCR amplification product was sent to Suzhou JGENEWIZ Biotechnology Co., Ltd. for sequencing. The sequencing results were uploaded to the National Center for Biotechnology Information (NCBI) database for a BLAST comparison and the strain was found to be *Pichia kudriavzevii*.

The strain DC-16 was preliminarily identified as a *Pichia kudriavzevii* DC-16 by comprehensive colony morphological characteristics, physiological and biochemical characteristics and ITS sequence analysis. The strain has been deposited in the China General Microbiological Culture Collection Center whose address is No. 3, Courtyard 1, West Beichen Road, Chaoyang District, Beijing and has a deposit number of CGMCC NO. 19337.

Example 3

Degradation of Lactic Acid by Yeast of the Present Disclosure

A sorghum juice medium containing lactic acid of different concentrations was used as a fermentation medium, and an experimental strain *Pichia kudriavzevii* DC-16 (P.k. DC-16) and a type strain *Pichia kudriavzevii* ATCC 24210 (P.k. ATCC 24210) were used for a lactic acid metabolic experiment. According to detection results of lactic acid in fermented grains during a screening process, the amount of the lactic acid in the designed metabolic experiment was 20, 30, and 40 g·$L^{-1}$ separately.

Experimental groups and control groups were arranged as follows:

Control group 1: inoculating P.k. ATCC 24210 into a sorghum juice medium containing 20 g·$L^{-1}$ lactic acid at an inoculum size of 7% (v:v);

Experimental group 1: inoculating P.k. DC-16 into a sorghum juice medium containing 20 g·$L^{-1}$ lactic acid at an inoculum size of 7% (v:v);

Control group 2: inoculating P.k. ATCC 24210 into a sorghum juice medium containing 30 g·$L^{-1}$ lactic acid at an inoculum size of 7% (v:v);

Experimental group 2: inoculating P.k. DC-16 into a sorghum juice medium containing 30 g·$L^{-1}$ lactic acid at an inoculum size of 7% (v:v);

Control group 3: inoculating P.k. ATCC 24210 into a sorghum juice medium containing 40 g·$L^{-1}$ lactic acid at an inoculum size of 7% (v:v); and Experimental group 3: inoculating P.k. DC-16 into a sorghum juice medium containing 40 g·$L^{-1}$ lactic acid at an inoculum size of 7% (v:v).

The type strain P.k. ATCC 24210 was purchased from the China General Microbiological Culture Collection Center and has a deposit number of CGMCC 2.1465. The sorghum juice medium containing lactic acid was adjusted to a pH of 3.5 (a pH of real fermented grains) with 5 M NaOH and the strains were inoculated into the medium at an inoculum size of 7% (v:v) and cultured at 30° C. and 200 rpm for 72 h. Samples were taken every 12 h to determine the content of lactic acid and $OD_{600}$ in the fermentation broth.

Figure 1B:
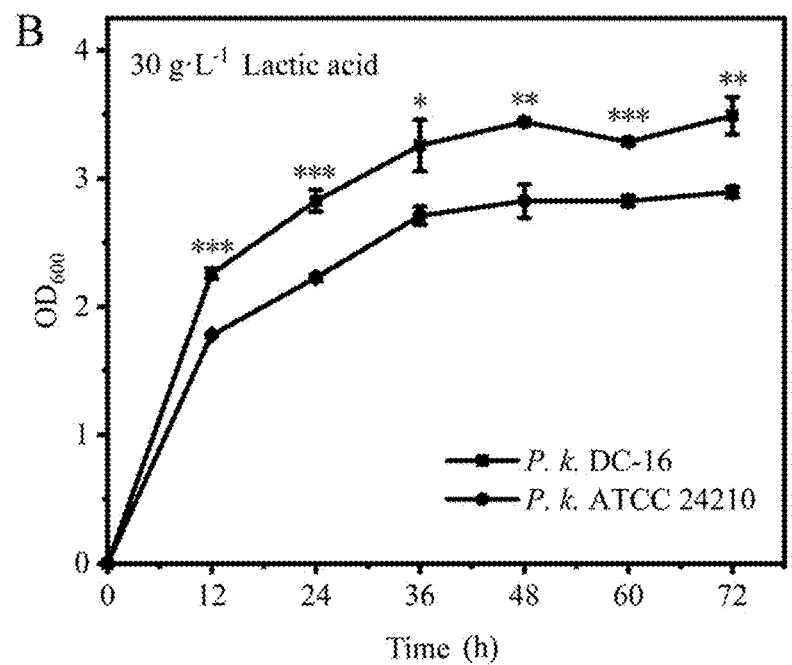
FIG. 1B shows growth curves of an experimental strain and a type strain under 30 g $L^{-1}$ lactic acid.
Figure 1C:
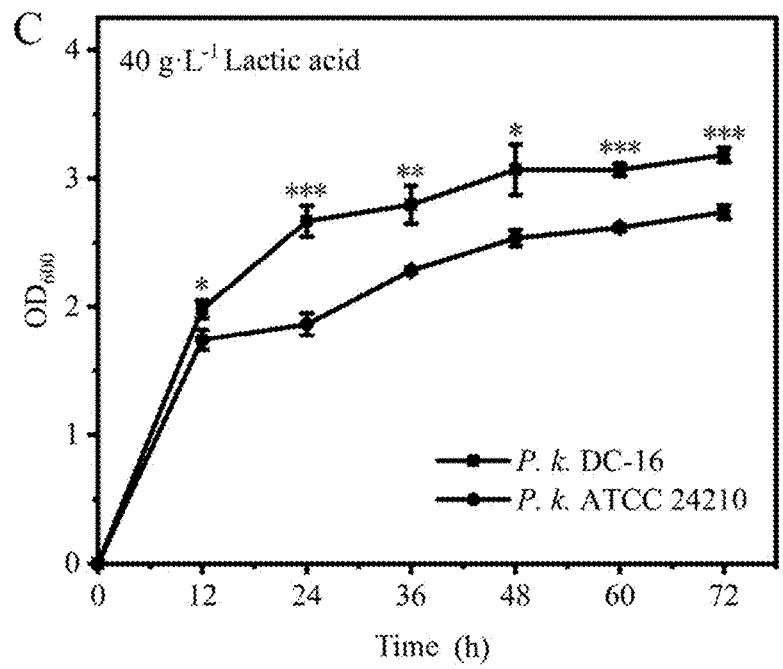
FIG. 1C shows growth curves of an experimental strain and a type strain under 40 g $L^{-1}$ lactic acid.
Figure 1D:
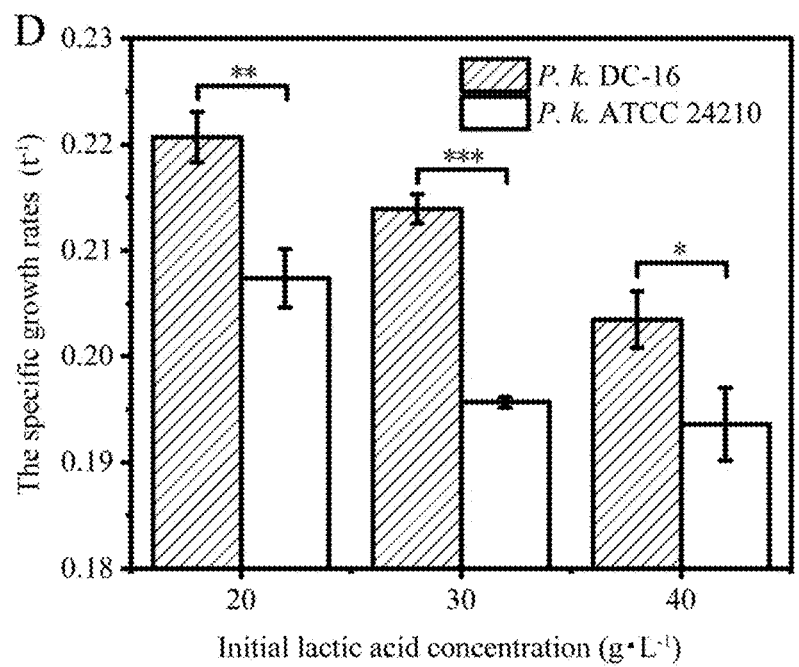
FIG. 1D shows specific growth rates of an experimental strain and a type strain under different concentrations of lactic acid.
Figure 2A:
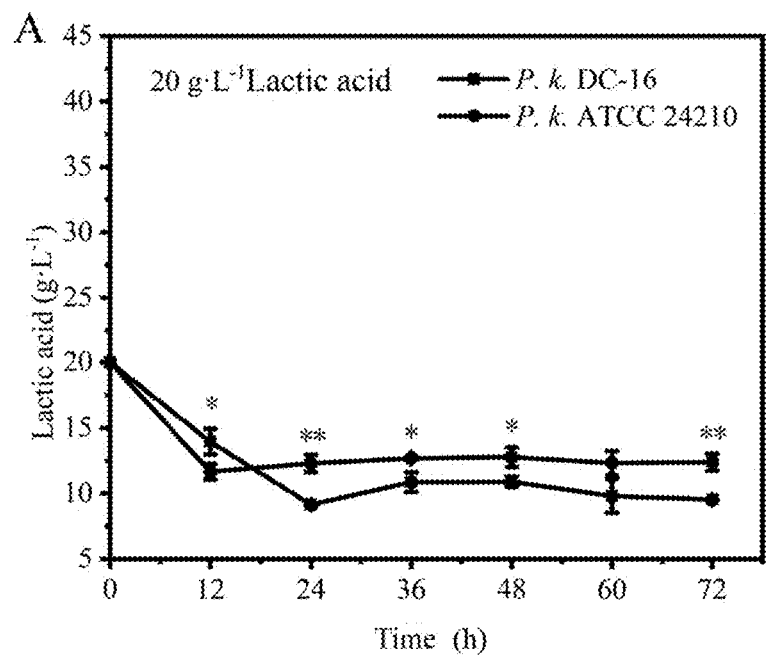
FIG. 2A shows a comparison of lactic acid consumption of an experimental strain and a type strain under 20 g $L^{-1}$ lactic acid.
Figure 2B:
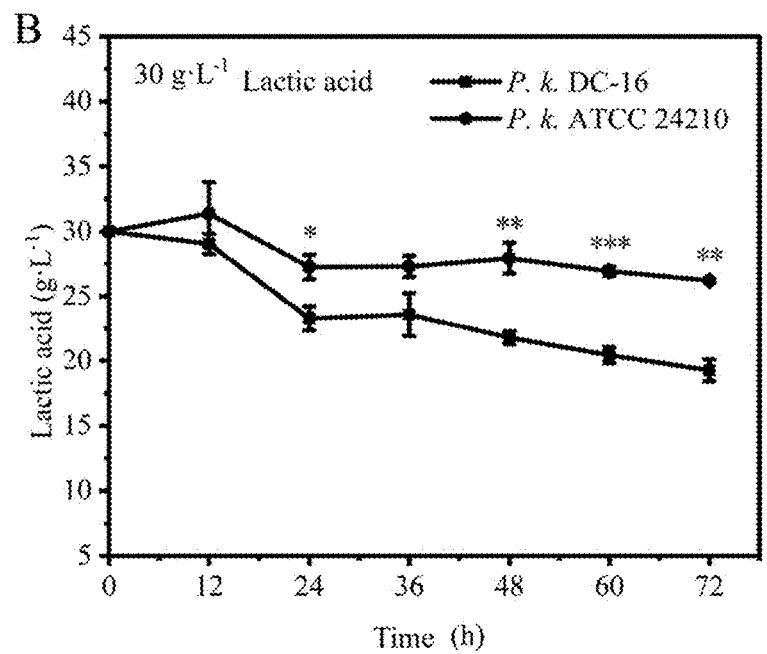
FIG. 2B shows a comparison of lactic acid consumption of an experimental strain and a type strain under 30 g $L^{-1}$ lactic acid.
Figure 2C:
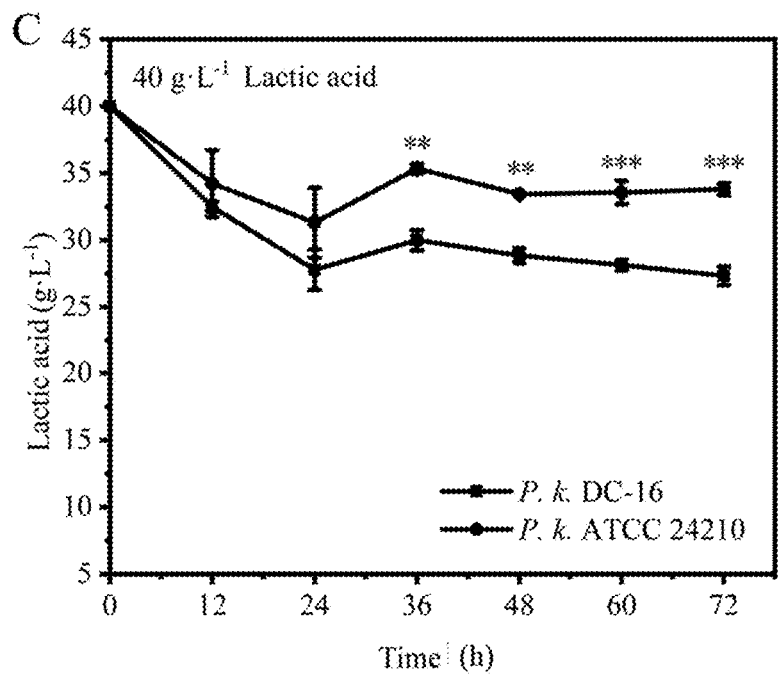
FIG. 2C shows a comparison of lactic acid consumption of an experimental strain and a type strain under 40 g $L^{-1}$ lactic acid.
Figure 2D:
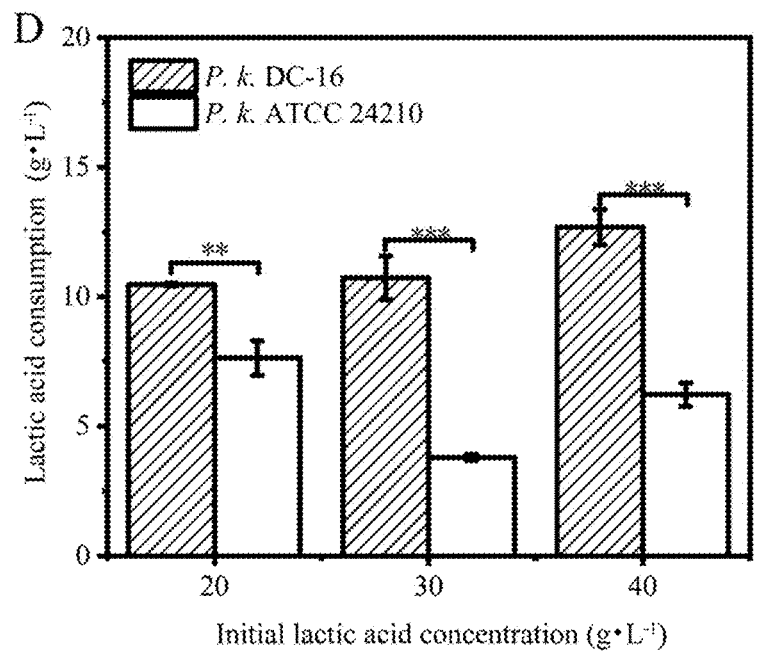
FIG. 2D shows lactic acid consumption amount of an experimental strain and a type strain under different concentrations of lactic acid.

The results showed that compared with the type strain P.k. ATCC 24210, the experimental strain P.k. DC-16 had a higher biomass at an end point and a faster specific growth rate. The specific results were as shown in FIG. 1A-FIG. 1C. The type strain P.k. ATCC 24210 had an end-point $OD_{600}$ of 3.32, 2.90 and 2.74 separately under 20, 30, and 40 g·$L^{-1}$ lactic acid stress; and the experimental strain P.k. DC-16 had an end-point $OD_{600}$ of 3.81, 3.49 and 3.18 separately under 20, 30, and 40 g·$L^{-1}$ lactic acid stress, which was 1.14, 1.20 and 1.16 times that of the type strain separately. The type strain P.k. ATCC 24210 had a specific growth rate of 0.2074, 0.1956 and 0.1936 $t^{-1}$ separately under 20, 30, and 40 g·$L^{-1}$ lactic acid stress; and the experimental strain P.k. DC-16 had a specific growth rate of 0.2207, 0.2139 and 0.2035 t$^{-1}$ separately under 20, 30, and 40 g·L$^{-1}$ lactic acid stress, which was 1.06, 1.09 and 1.05 times that of the type strain separately (FIG. 1D). The above results indicated that the P.k. DC-16 had a higher lactic acid tolerance and was more suitable for a production process of high-lactic acid environment.

Compared with the type strain P.k. ATCC 24210, the experimental strain P.k. DC-16 could degrade more lactic acid. The specific results were as shown in FIG. 2A-FIG. 2D. When the sorghum juice medium separately contained 20, 30, and 40 g·L$^{-1}$ lactic acid, the type strain P.k. ATCC 24210 could degrade 7.62, 3.80 and 6.21 g·L$^{-1}$ lactic acid separately; and the experimental strain P.k. DC-16 could degrade 10.48, 10.73 and 12.69 g·L$^{-1}$ lactic acid separately, which was 1.37, 2.83 and 2.04 times that of the type strain separately.

Figure 3A:
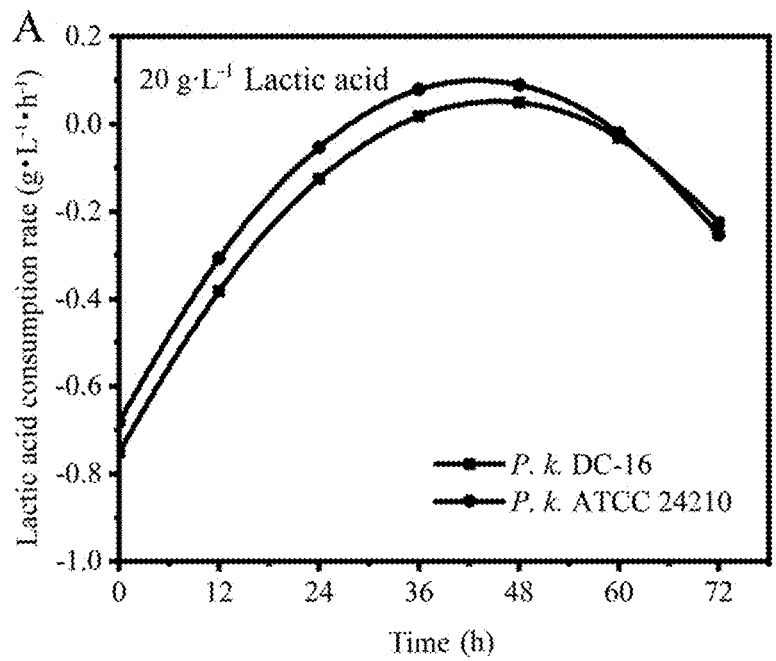
FIG. 3A shows a comparison of lactic acid consumption rates of an experimental strain and a type strain under 20 g $L^{-1}$ lactic acid.
Figure 3B:
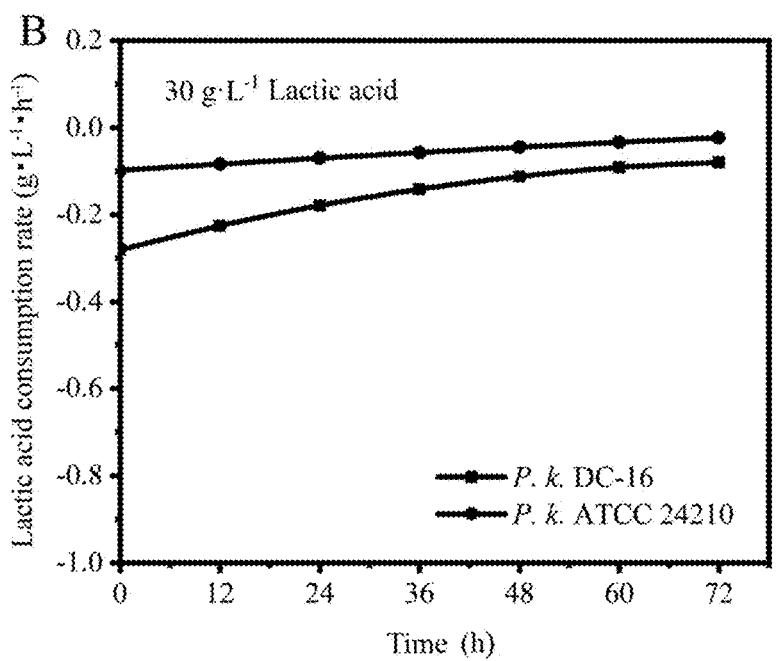
FIG. 3B shows a comparison of lactic acid consumption rates of an experimental strain and a type strain under 30 g $L^{-1}$ lactic acid.
Figure 3C:
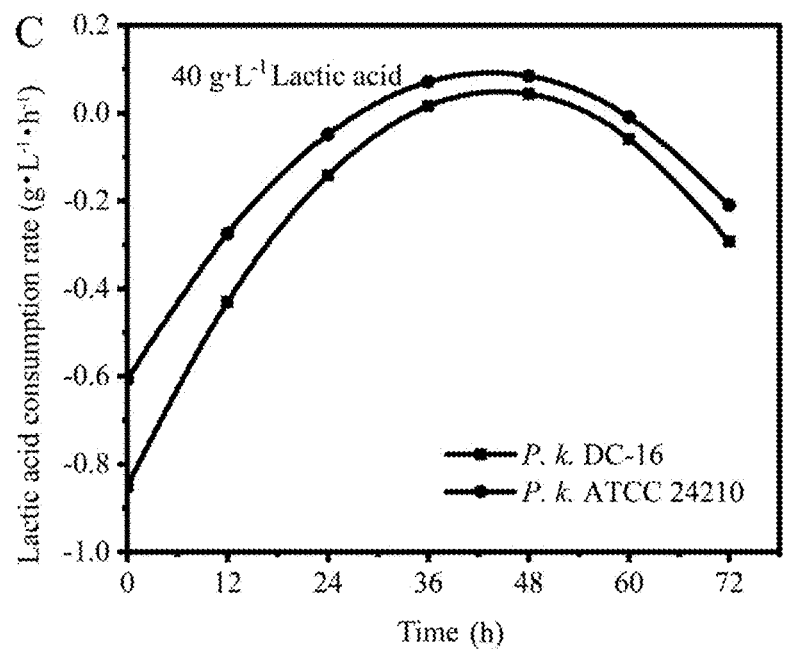
FIG. 3C shows a comparison of lactic acid consumption rates of an experimental strain and a type strain under 40 g $L^{-1}$ lactic acid.

Compared with the type strain P.k. ATCC 24210, the experimental strain P.k. DC-16 had a higher rate for degrading lactic acid. The specific results were as shown in FIG. 3A-FIG. 3C. After 12 h of fermentation, a consumption rate of lactic acid was the highest. When the sorghum juice medium separately contained 20, 30 and 40 g·L$^{-1}$ lactic acid, the type strain P.k. ATCC 24210 had a lactic acid consumption rate of 0.31, 0.08 and 0.27 g·L$^{-1}$h$^{-1}$ separately; and the experimental strain P.k. DC-16 had a lactic acid consumption rate of 0.38, 0.22 and 0.43 g·L$^{-1}$h$^{-1}$, which was 1.24, 2.70 and 1.57 times that of the type strain separately.

Example 4

Complex Microbial Inoculant for Degrading Lactic Acid

A sorghum juice medium containing 40 g·L$^{-1}$ lactic acid was used as a fermentation medium and an independent or combined fermentation experiment was conducted on an experimental strain P.k. DC-16 and *Saccharomyces cerevisiae* DC-3 (S.c. DC-3). The *Saccharomyces cerevisiae* DC-3 had deposited in the China General Microbiological Culture Collection Center on Jan.13, 2020 and had a deposit number of CGMCC NO. 19336.

Control group 1: Seed liquid of P.k. DC-16 was inoculated into a sorghum juice medium with an inoculum size of a final concentration of 2×10$^7$ cells·mL$^{-1}$ and 40 g·L$^{-1}$ lactic acid was added.

Control group 2: Seed liquid of S.c. DC-3 was inoculated into a sorghum juice medium with an inoculum size of a final concentration of 2×10$^7$ cells·mL$^{-1}$ and 40 g·L$^{-1}$ lactic acid was added.

Experimental group: Seed liquids of P.k. DC-16 and S.c. DC-3 were inoculated into a sorghum juice medium with an inoculum size of 10$^7$ cells·mL$^{-1}$ separately and 40 g·L$^{-1}$ lactic acid was added.

The fermentation culture was conducted at 30° C. and 200 rpm for 72 h. Samples were taken every 12 h to determine the biomass and the ethanol and lactic acid content of the two yeasts in the fermentation broth were determined.

Figure 6:
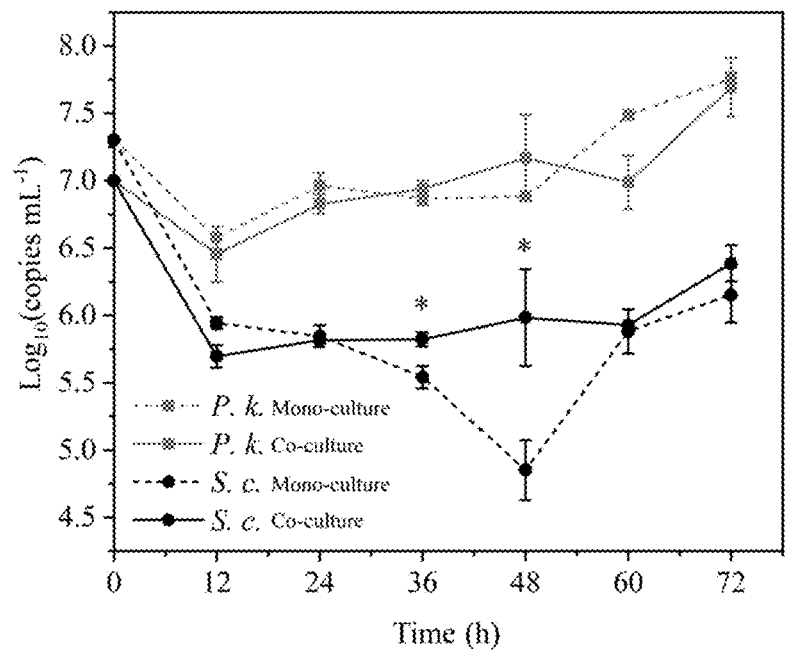
FIG. 6 shows a comparison of biomass of mono-culture (*Pichia kudriavzevii* DC-16) and co-culture (*Pichia kudriavzevii* DC-16 and *Saccharomyces cerevisiae* DC-3) under lactic acid stress.

The biomass of the P.k. DC-16 and the S.c. DC-3 during mono-culture and co-culture was shown in FIG. 6. Due to a toxic effect of high-concentration lactic acid on yeast, the biomass of the P.k. DC-16 and the S.c. DC-3 decreased in both mono-culture and co-culture at an early stage of fermentation.

When fermentation for 12 h, the P.k. DC-16 decreased from 2.0×10$^7$ cells·mL$^{-1}$ to 3.8×10$^6$ cells·mL$^{-1}$ during mono-culture and decreased from 1.0×10$^7$ cells·mL$^{-1}$ to 2.8×10$^6$ cells·mL$^{-1}$ during co-culture; and the biomass of the P.k. DC-16 slowly increased and reached a highest value at 72 h, where the end-point biomass of the mono-culture was 5.7× 10$^7$ cells·mL$^{-1}$ and the end-point biomass of the co-culture was 5.0×10$^7$ cells·mL$^{-1}$. The biomass of the P.k. DC-16 did not vary significantly between mono-culture and co-culture (P<0.05).

The S.c. DC-3 reached a minimum biomass of 7.1×10$^4$ cells·mL$^{-1}$ at 48 h during the mono-culture, while reached a minimum biomass of 5.0×10$^5$ cells·mL$^{-1}$ at 12 h during the co-culture due to a shortened lag phase, and the biomass remained stable afterwards. At 48 h, the S.c. DC-3 had a biomass (9.6×10$^5$ cells·mL$^{-1}$) in the co-culture, which was 13 times that in the mono-culture. The above results showed that the P.k. DC-16 utilized lactic acid, thus could relieve a stress effect of the lactic acid on wine-producing yeast in a brewing system, and could better conduct subsequent alcoholic fermentation.

Figure 7A:
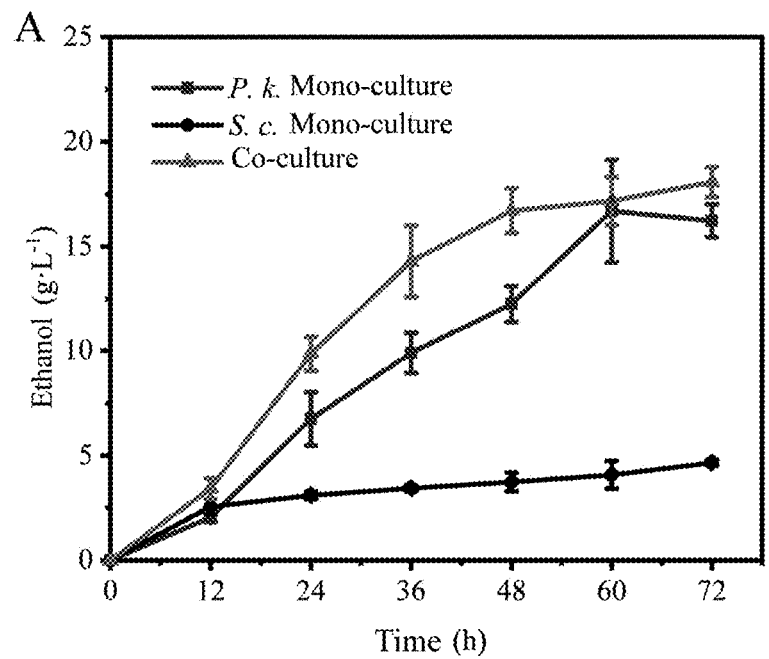
FIG. 7A shows a comparison of ethanol production amount of mono-culture (*Pichia kudriavzevii* DC-16) and co-culture (*Pichia kudriavzevii* DC-16 and *Saccharomyces cerevisiae* DC-3) under lactic acid stress.
Figure 7B:
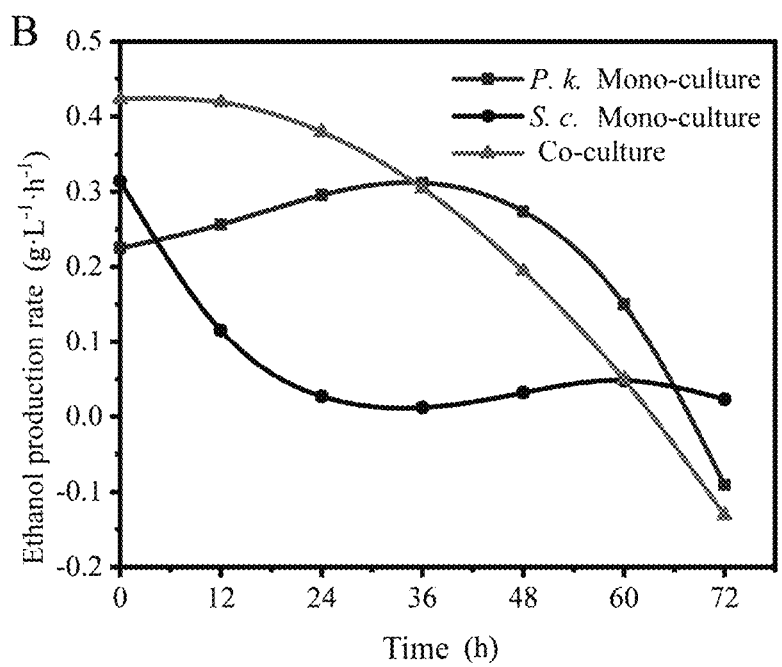
FIG. 7B shows a comparison of ethanol production rates of mono-culture (*Pichia kudriavzevii* DC-16) and co-culture (*Pichia kudriavzevii* DC-16 and *Saccharomyces cerevisiae* DC-3) under lactic acid stress.

The S.c. DC-3 had a severely inhibited ethanol-producing ability under 40 g·L$^{-1}$ lactic acid stress. As shown in FIG. 7A, at the end of the fermentation, the P.k. DC-16 had the ethanol yield of 16.23 g·L$^{-1}$, while the S.c. DC-3 had the ethanol yield of only 4.66 g·L$^{-1}$. When the P.k. DC-16 and the S.c. DC-3 were co-cultured, the ethanol yield was 18.08 g·L$^{-1}$, which was increased compared to that in the mono-culture. As shown in FIG. 7B, an ethanol production rate of the P.k. DC-16 in the mono-culture was 0.26 g·L$^{-1}$h$^{-1}$ at 12 h of fermentation and the ethanol production rate of the S.c. DC-3 in the mono-culture was 0.21 g·L$^{-1}$h$^{-1}$ at 12 h of the mono-culture. The ethanol production rate was 0.42 g·L$^{-1}$h$^{-1}$ in the co-culture, which was 1.64 and 3.64 times that of the P.k. DC-16 in the mono-culture and the S.c. DC-3 in the mono-culture separately. The co-culture of the P.k. DC-16 and S.c. DC-3 could improve the yield and the production rate of ethanol compared with the mono-culture of the single strain.

Figure 8A:
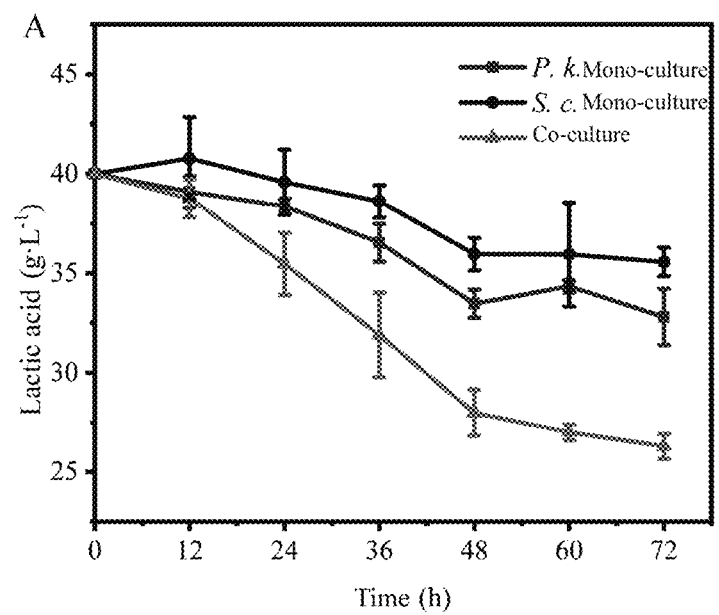
FIG. 8A shows a comparison of lactic acid consumption of mono-culture (*Pichia kudriavzevii* DC-16) and co-culture (*Pichia kudriavzevii* DC-16 and *Saccharomyces cerevisiae* DC-3) under lactic acid stress.
Figure 8B:
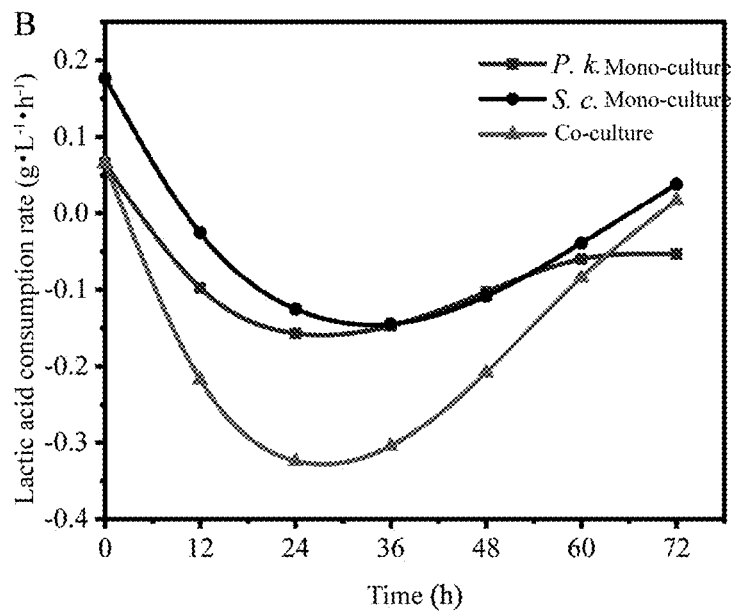
FIG. 8B shows a comparison of lactic acid consumption rates of mono-culture (*Pichia kudriavzevii* DC-16) and co-culture (*Pichia kudriavzevii* DC-16 and *Saccharomyces cerevisiae* DC-3) under lactic acid stress.

As shown in FIG. 8A, at the end of the fermentation, the P.k. DC-16 could utilize 7.20 g·L$^{-1}$ of lactic acid in the medium and the S.c. DC-3 could utilize 4.44 g·L$^{-1}$ of lactic acid. However, when the P.k. DC-16 and S.c. DC-3 were co-cultured, the content of lactic acid in the medium decreased by 13.71 g·L$^{-1}$ and the degrading amount of lactic acid increased significantly (P<0.01). As shown in FIG. 8B, the P.k. DC-16 had a maximum consumption rate of lactic acid at 0.16 g·L$^{-1}$h$^{-1}$ and the S.c. DC-3 had a maximum consumption rate of lactic acid at 0.15 g·L$^{-1}$h$^{-1}$. However, the maximum consumption rate of lactic acid was significantly increased during co-culture (0.32 g·L$^{-1}$h$^{-1}$). This indicated that the co-culture of the P.k. DC-16 and the S.c. DC-3 could enhance the ability of the yeast to utilize the lactic acid compared with the mono-culture.

A gene IIdD encodes a lactate dehydrogenase capable of degrading lactic acid to pyruvate and is a key gene involved in degrading lactic acid. Transcription of the gene IIdD of the P.k. DC-16 and the S.c. DC-3 in the co-culture was shown in Table 1. When cultured for 12 h, only the P.k. DC-16 transcribed the gene IIdD, while the S.c. DC-3 did not transcribe the gene IIdD, indicating that when the lactic acid concentration was high, only the P.k. DC-16 was involved in degrading lactic acid. When culture was conducted for 24 h, the concentration of lactic acid in the medium decreased to 35.46 g·L$^{-1}$ and both the P.k. DC-16 and the S.c. DC-3 transcribed the gene IIdD, indicating that at a low concentration of lactic acid, the P.k. DC-16 and the S.c. DC-3 participated in degrading lactic acid together.

TABLE 1

Transcription of gene IldD of two yeast strains in co-culture

| Culturing time (h) | P.k. DC-16 | S.c. DC-3 |
|---|---|---|
| 12 | + | − |
| 24 | + | + |

Note:
"+" indicated that the transcription of the gene IldD was detected in the sample, while "−" indicated that the transcription of the gene was not detected.

Example 5

Use of Complex Microbial Inoculant in Reducing Lactic Acid in Fermentation Process of Baijiu A *Pichia kudriavzevii* DC-16 was inoculated into a sorghum juice liquid medium and incubated at a constant temperature of 30° C. for 48 h under shaking. The strain-containing liquid medium was centrifuged at 12,000 r/min for 10 min, a supernatant was discarded, a cell precipitate of the strain was obtained and washed with sterile water for several times, and the concentration of yeast liquid was calculated by using a hemocytometer for standby use.

Figure 9:
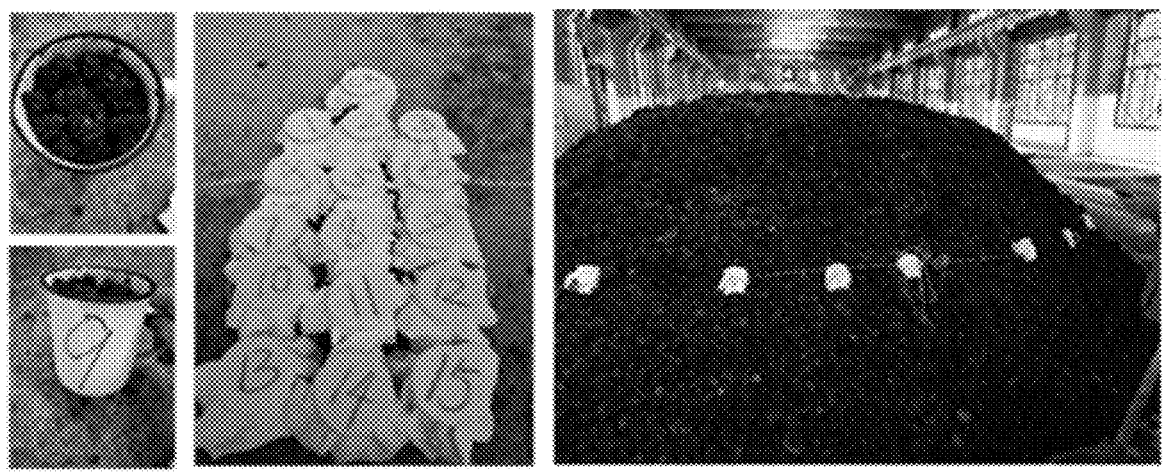
FIG. 9 shows use of a *Pichia kudriavzevii* DC-16 and a microbial inoculant thereof in a production process of soy sauce-aroma baijiu.

An experiment of use of the strain in one round of soy sauce-aroma baijiu fermentation was shown in FIG. 9. When Daqu was added into fermented grains, the strain liquid was added with the amount of $10^6$ CFU/kg of the fermented grains; and the same amount of distilled water was added as a control group. Each group was tested in triplets. Two groups of the fermented grains were loaded into enamel jars and buried in fermented grains subjected to stacking fermentation for in-situ fermentation, sampling was conducted at the end of the stacking fermentation, and the lactic acid content of the fermented grains was detected.

After testing, the lactic acid content in the fermented grains of the control group was 12.01 g/kg fermented grains and the lactic acid content in the fermented grains containing the *Pichia kudriavzevii* DC-16 was 7.55 g/kg fermented grains, and a degradation rate of lactic acid was 37.09%. At the same time, the ethanol content in the fermented grains of the control group was 15.12 g/kg fermented grains, which was not significantly different from that in the fermented grains containing the *Pichia kudriavzevii* DC-16. Therefore, the *Pichia kudriavzevii* DC-16 can tolerate and reduce the lactic acid content during a fermentation process without affecting a metabolic function of ethanol.

Example 6

Inhibition on Growth of Undesired Microorganisms by *Pichia kudriavzevii* DC-16 and Complex Microbial Inoculant Thereof In order to verify an ecological regulation effect of *Pichia* on imbalanced flora, use of functional flora in production was further conducted. A *Pichia kudriavzevii* DC-16, a *Saccharomyces cerevisiae* DC-3 and a complex microbial inoculant with an equal proportion of the two strains were selected as compound inoculants. A team with low alcohol yield historically was selected for an adding experiment. When Daqu was added to fermented grains, the yeast strain liquid was evenly sprayed on surfaces of the fermented grains with a final amount of $10^6$ CFU/kg of the fermented grains; and the same amount of distilled water was added as a control group. Each group was tested in triplets. Two groups of the fermented grains were loaded into enamel jars and buried in fermented grains subjected to stacking fermentation for in-situ fermentation, sampling was conducted at the end of the stacking fermentation, and comparative analysis of a microbial structure of the fermented grains was conducted.

Figure 10:
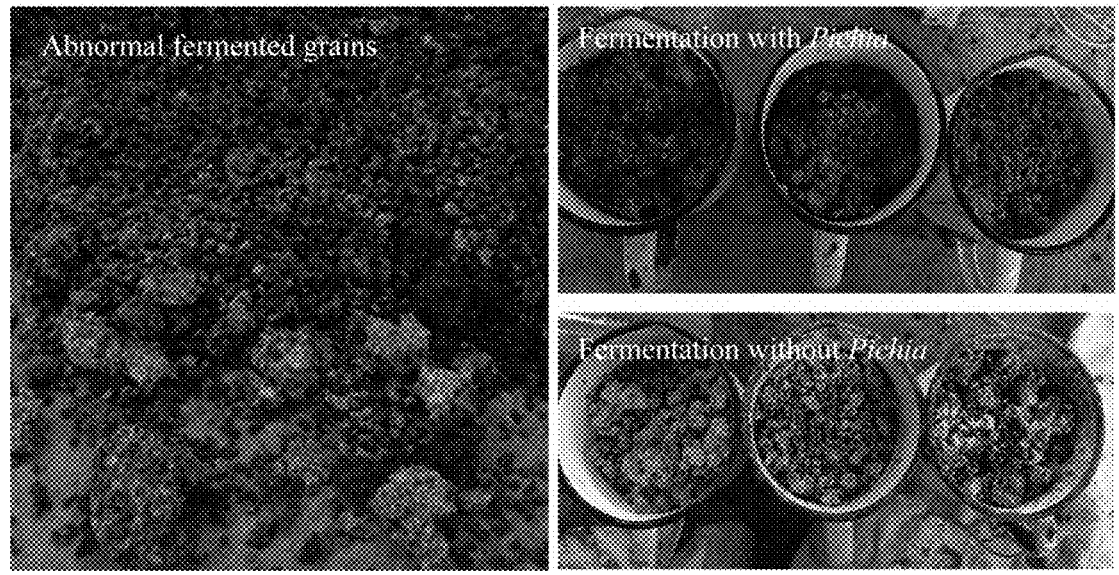
FIG. 10 shows an effective inhibitory effect of *Pichia kudriavzevii* DC-16 on mold outbreak during a baijiu fermentation process.

The results showed that the team in the experiment was abnormal and the in-situ fermented grains agglomerated more seriously. The fermented grains in an experimental group not containing *Pichia* also agglomerated in the enamel jar; the fermented grains in an experimental group containing *Saccharomyces cerevisiae* alone did not show a significant effect; while the fermented grains in an experimental group containing *Pichia* were loose and did not agglomerate (FIG. 10). The analysis of the microbial structure showed that the *Pichia* contained in the experimental group could significantly inhibit growth of filamentous fungi. The main microorganism in the fermented grains was the *Pichia* and had a structure similar to the microorganism in the normal fermented grains. The fermented grains in the agglomeration group were mainly composed of *Monascus* and showed obvious mildew and agglomeration. Combined with analysis of physical and chemical indicators, there was no significant difference in the ethanol content between the group containing *Pichia* and the control group, while the content of acetic acid and lactic acid could be significantly reduced, which is important for maintaining proliferation of *Saccharomyces cerevisiae* in fermentation of baijiu.

Example 7

Use of Complex Microbial Inoculant in Maintenance of Ecological Restoration

A complex microbial inoculant in inhibiting *Streptomyces* and geosmin was used as an example.

Figure 11:
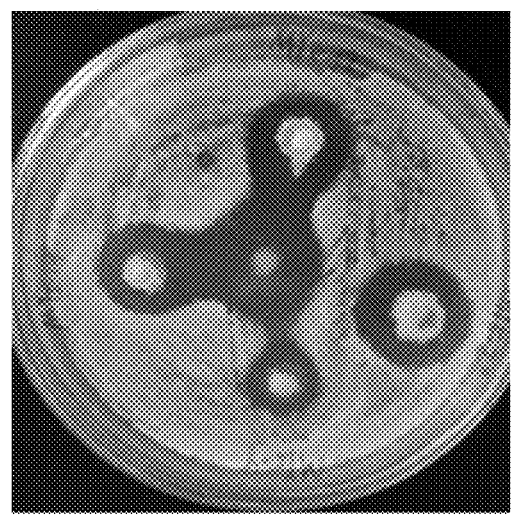
FIG. 11 shows an inhibitory effect of a *Pichia kudriavzevii* DC-16 on *Streptomyces albus*.

Inhibition on growth of the Streptomyces by a *Pichia kudriavzevii* DC-16 was determined. The growth inhibition was quantified as size of zone of inhibition, that is, a diameter ratio of zone of inhibition to colony (R zone of inhibition/R colony). The size of zone of inhibition was observed by a filter paper method of a Kirby-Bauer (K-B) test and an inhibitory effect of the *Pichia kudriavzevii* was preliminarily determined. As shown in FIG. 11, 100 mL of $10^6$ CFU/L *Streptomyces* was evenly spread on a plate and 10 mL of $10^6$ CFU/L yeast liquid was inoculated on filter paper. A result preliminarily showed that the *Pichia kudriavzevii* DC-16 had an inhibitory effect on *Streptomyces albus* in traditional Xifeng aroma Daqu.

Figure 12A:
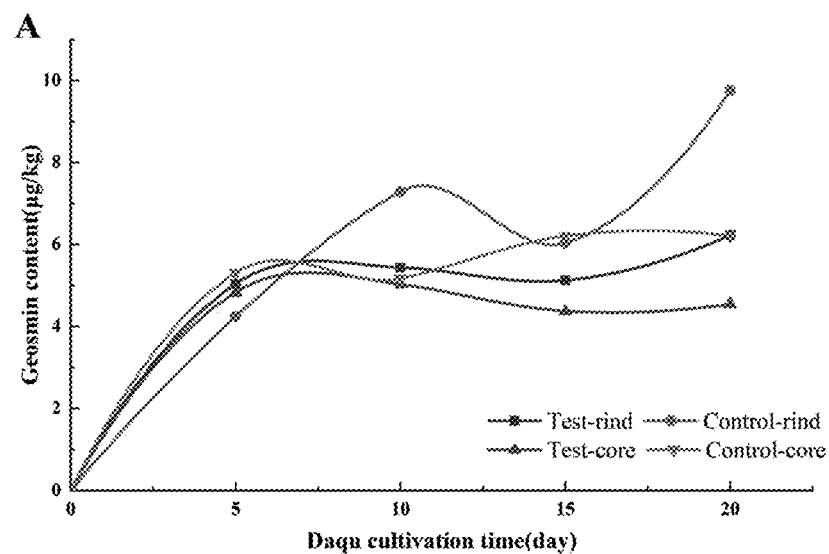
FIG. 12A shows an effect of a *Pichia kudriavzevii* DC-16 inoculant on geosmin (the content of geosmin in rind and core of Daqu) in a cultivation process of Daqu.

In production of the Daqu, 6 strains of *Pichia fermentans, Pichia kudriavzevii* DC-16, *Saccharomyces cerevisiae, Issatchenkia orientalis* and *Bacillus subtilis* with a significant anti-microbial effect were selected and separately prepared into an anti-microbial agent with the same concentration. When raw materials of the Daqu were blended, a complex microbial inoculant was added to a final concentration of $10^6$ CFU/kg of the Daqu material, the material was pressed into blocks and labeled, and the blocks were put into a Daqu room for fermentation. Samples were collected on the day 0, 3, 5, 10, 15 and 20. The content of geosmin in a control group and an experimental group showed similar dynamic characteristics in rind and core of the Daqu. In the rind of the Daqu, the content of the geosmin increased rapidly in both groups in an early stage and a middle stage, fluctuated and decreased around the 15th day. But the content of the geosmin fluctuated slightly in the experimental group compared with that in the control group. The content of the geosmin was the highest in the control group on the 20th day and reached 9.75 µg/kg; and the content of the geosmin was 6.23 µg/kg in the experimental group, which is significantly lower than that of the control group (FIG. 12A). The microorganism had an average inhibitory rate of the geosmin of 14.4% in rind of Daqu and a final inhibitory rate of 36.1%.

Figure 12B:
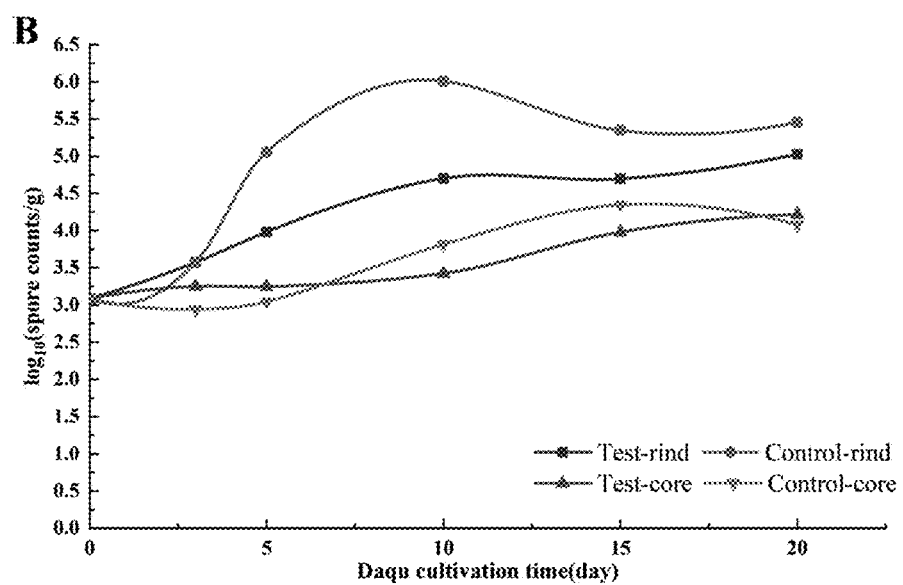
FIG. 12B shows an effect of a *Pichia kudriavzevii* DC-16 inoculant on *Streptomyces albus* (the content of *Streptomyces albus* in rind and core of Daqu) in a cultivation process of Daqu.

A real-time quantitative PCR (qPCR) analysis was used to monitor the dynamic biomass of *Streptomyces albus* during a fermentation process. The dynamic changes of the biomass of all *Streptomyces albus* during the Daqu fermentation process were shown in FIG. 12B. In the rind of the Daqu, the biomass of the *Streptomyces albus* in the control group was 5.46 $\log_{10}$ (spore counts/g) at the end of the cultivation. In the experimental group, the biomass of the *Streptomyces albus* was 5.03 $\log_{10}$ (spore counts/g) at the end of the cultivation. In the core of the Daqu, the biomass of the *Streptomyces albus* was 4.08 $\log_{10}$ (spore counts/g) in the control group at the end of the cultivation. In the experimental group, the biomass of the *Streptomyces albus* was 4.21 $\log_{10}$ (spore counts/g) at the end of the cultivation. It can be seen that the geosmin-inhibiting inoculant had a better inhibitory effect on geosmin-producing *Streptomyces albus* in the rind of the Daqu than in the core of the Daqu, and a better inhibitory effect in the early and middle stages of the Daqu making than in the late stage of the Daqu making.

Example 8

Use of *Pichia kudriavzevii* DC-16 in Field of Food Preservation

Figure 13:
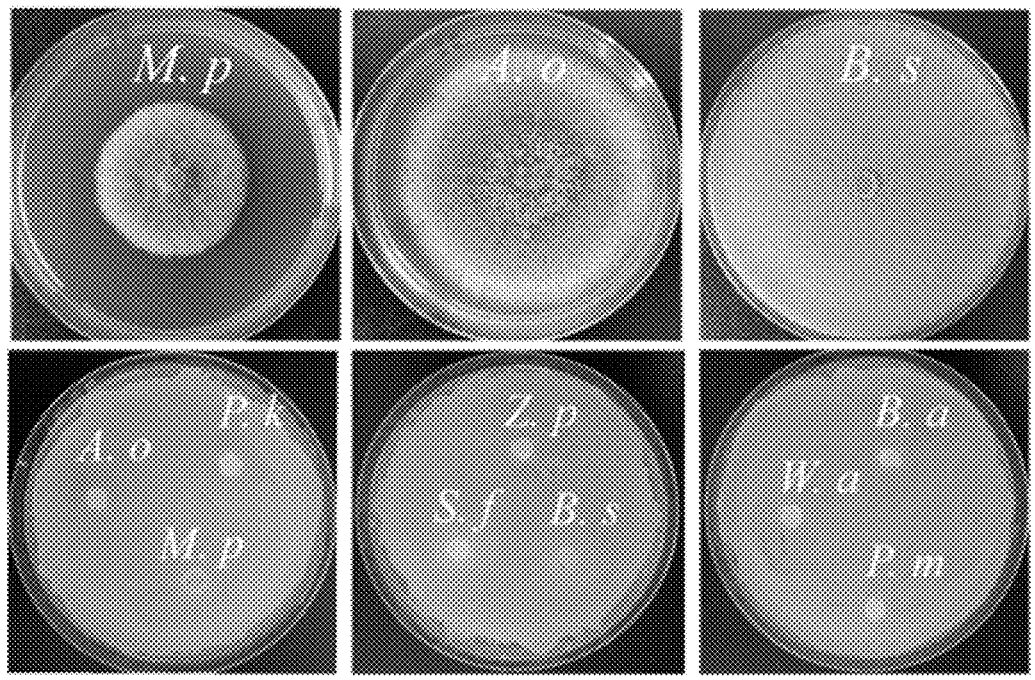
FIG. 13 shows an inhibitory effect of a *Pichia kudriavzevii* DC-16 on common filamentous fungi.

Filamentous fungi are common contaminating microorganisms in a process of food preservation and can produce mycotoxins such as ochratoxin A, which are harmful to human health. A relationship between a *Pichia kudriavzevii* DC-16 and filamentous fungi was detected by an agar diffusion method. A piece of 5-mm sterile filter paper was placed in a middle of a PDA plate and the plate was evenly covered with 100 µL of the *Pichia kudriavzevii* ($10^6$ CFU/mL). 10 µL of culture liquid of filamentous fungi was dropped onto the filter paper. In a negative control, sterile filter paper and isolated microorganisms were placed in a middle of a blank PDA plate. After incubation at 30° C. for 120 h, it was confirmed that the *Pichia kudriavzevii* had a strong inhibitory effect on growth of the filamentous fungi (FIG. 13).

Figure 14A:
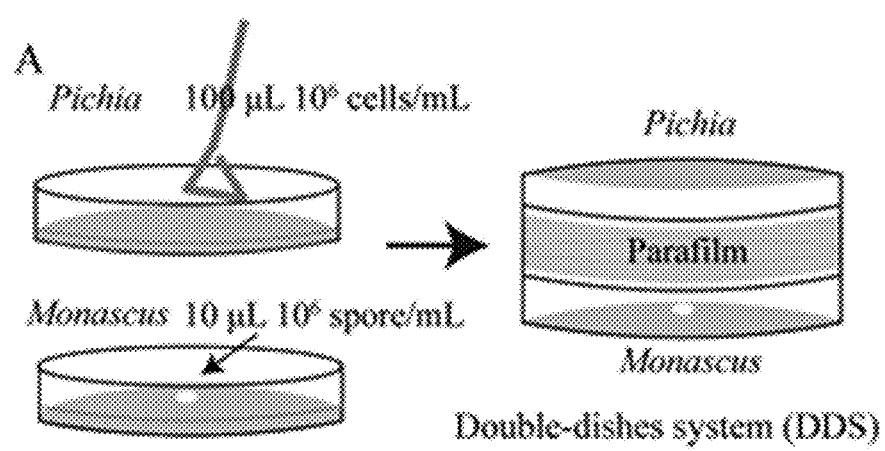
FIG. 14A shows an antifungal activity of volatile organic compounds produced by a *Pichia kudriavzevii* DC-16 inoculant; *Pichia* and *Monascus* are inoculated to prepare a double-dish system; and a dispersal distance of the Monascus on no-control sorghum extract agar and on a sorghum medium with the Pichia (+Pichia) in the double-dish system is determined daily.
Figure 14B:
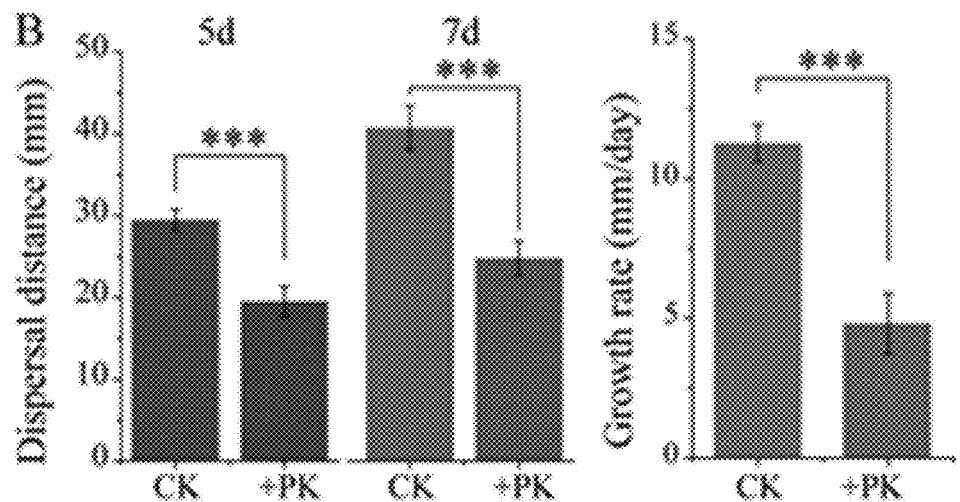
FIG. 14B shows an antifungal activity of volatile organic compounds produced by a *Pichia kudriavzevii* DC-16 inoculant; effects of the *Pichia* on a radial growth and a growth rate of *Monascus*; and a dispersal distance of the *Monascus* on no-control sorghum extract agar and on a sorghum medium with the *Pichia* (+*Pichia*) in the double-dish system is determined daily.

Further analysis showed that the *Pichia kudriavzevii* DC-16 could produce a volatile substance (VOC)-mediated antifungal property. A double-dish system (DDS) of sorghum extract agar was used to determine whether yeast can produce VOCs to affect growth of *Monascus* (FIG. 14A). The antagonism was reflected in a significant reduced growth of mycelia cultured at 30° C. (P0.05). The results were shown in FIG. 14B, a growth rate of *Monascus* in a control group on the sorghum extract agar plate was 11.26±0.67 $mmd^{-1}$; and the *Pichia* significantly reduced a growth rate of *Monascus* (4.80±1.07 $mmd^{-1}$).

Example 9

Use of *Pichia kudriavzevii* DC-16 in Maintaining Homeostasis of Yeast

Figure 15:
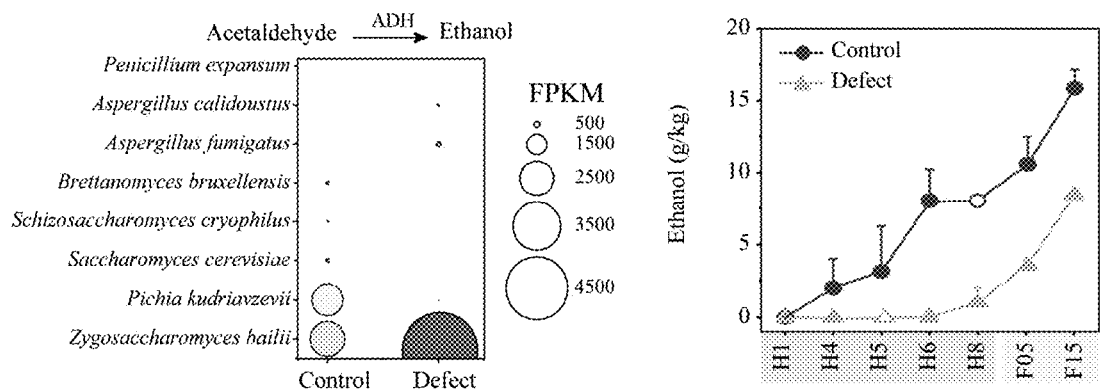
FIG. 15 shows effects of *Pichia kudriavzevii* on ethanol metabolism during a fermentation process; and Control (normal fermentation group): *Pichia kudriavzevii* as a dominant microorganism; and defect (abnormal fermentation group): filamentous fungi as a dominant microorganism.

During normal baijiu fermentation, a *Pichia kudriavzevii* DC-16 was dominated. Abnormally fermented grains showed agglomeration and mildew. A metatranscriptome analysis was used to compare ethanol-producing enzymes and genes to verify effects of the *Pichia kudriavzevii* DC-16 on functions and homeostasis of yeast flora during a baijiu fermentation process (FIG. 15). In a control group, yeasts (including *P. kudriavzevii, Z. bailii, Saccharomyces cerevisiae, Schizosaccharomyces cryophilus* and *Brettanomyces bruxellensis*) were major functional contributors to produce ethanol (FPKM >100). Meanwhile, in the abnormal fermentation group, *Zygosaccharomyces bailii* and filamentous fungi (*Aspergillus fumigatus, Aspergillus calidoustus* and *Penicillium expansum*) had abundant ADH gene expressions (FPKM >100). ADH in different microorganisms exhibited different metabolic abilities to form ethanol, which explained variation in ethanol content between samples during production. This indicated that a *Pichia*-driven community was beneficial to maintain yeast diversity and ethanol metabolism.

Although the disclosure has been disclosed as above in the preferred examples, it is not intended to limit the disclosure. Any person skilled in the art can make various changes and modifications without departing from the spirit and scope of the disclosure. Therefore, the protection scope of the disclosure should be as defined in the claims.

What is claimed is:

1. A method for degrading lactic acid, comprising using a *Pichia kudriavzevii* DC-16 and a *Saccharomyces cerevisiae* DC-3, or a microbial preparation containing the *Pichia kudriavzevii* DC-16 and the *Saccharomyces cerevisiae* DC-3 as a fermentation agent to degrade lactic acid in a fermentation process;
   wherein the *Pichia kudriavzevii* DC-16 has been deposited in the China General Microbiological Culture Collection Center on Jan. 13, 2020 and has a deposit number of CGMCC NO.19337; and
   the *Saccharomyces cerevisiae* DC-3 has been deposited in the China General Microbiological Culture Collection Center on Jan. 13, 2020 and has a deposit number of CGMCC NO.19336.

2. The method according to claim 1, wherein the fermentation agent is inoculated into a culture medium, lactic acid is added, and culture is conducted at 28-32° C. and 180-220 rpm for 60-100 h.

3. The method according to claim 2, wherein the medium is a sorghum juice medium.

4. The method according to claim 1, wherein the *Pichia kudriavzevii* DC-16 and the *Saccharomyces cerevisiae* DC-3 have an inoculation concentration ratio of 1:1.

* * * * *